United States Patent [19]
Snitman et al.

[11] Patent Number: 5,641,630
[45] Date of Patent: Jun. 24, 1997

[54] METHOD AND KIT FOR PERFORMING NUCLEIC ACID HYBRIDIZATION ASSAYS

[75] Inventors: David L. Snitman, Boulder, Colo.; Stephen D. Stroupe, Libertyville, Ill.

[73] Assignees: Amgen Inc., Thousand Oaks, Calif.; Abbott Laboratories, North Chicago, Ill.

[21] Appl. No.: 429,864

[22] Filed: Apr. 27, 1995

Related U.S. Application Data

[63] Continuation of Ser. No. 136,446, Oct. 14, 1993, abandoned, which is a continuation of Ser. No. 798,027, Nov. 20, 1991, Pat. No. 5,273,882, which is a continuation of Ser. No. 512,092, Apr. 11, 1990, abandoned, which is a continuation of Ser. No. 170,173, Mar. 14, 1988, abandoned, which is a continuation of Ser. No. 744,800, Jun. 13, 1985, abandoned.

[51] Int. Cl.$^6$ .................................................. C12Q 1/68
[52] U.S. Cl. ................................ 435/6; 935/77; 935/78
[58] Field of Search ............................. 435/6; 935/77, 935/78

[56] References Cited

U.S. PATENT DOCUMENTS

| | | | |
|---|---|---|---|
| 4,486,539 | 12/1984 | Ranki et al. | 435/6 |
| 4,766,062 | 8/1988 | Diamond et al. | 435/6 |
| 5,030,557 | 7/1991 | Hogan et al. | 435/6 |

FOREIGN PATENT DOCUMENTS

| | | | |
|---|---|---|---|
| 0192168 | 8/1986 | European Pat. Off. | 435/6 |

OTHER PUBLICATIONS

Matthews et al., Anal. Biochem. 169:1–25 (1988).
Langer et al. PNAS (USA) 78(11):6633–6637 (Nov. 1981).
Ranki et al. Gene 21:77–85 (1983).

*Primary Examiner*—Stephanie W. Zitomer
*Attorney, Agent, or Firm*—Marshall, O'Toole, Gerstein, Murray & Borun

[57] ABSTRACT

A method and a kit for the isolation and quantitative detection of a selected target nucleic acid sequence from solution employing two probes. A first probe is complementary to one portion of the target and is covalently attached to a first complexing agent (e.g., either an antigen or an antibody). The second probe is complementary to a different portion of the target and is associated with a reporter group. Following hybridization of the target and two probes in solution, a solid support coated with a second complexing agent (i.e., a corresponding antibody or antigen) capable of binding to the first complexing agent on the first probe is employed to immobilize the target-probe hybrid complex.

A plurality of types of first probes may be used. Each type is attached to the same sort of complexing agent but each includes a nucleic acid sequence which is complementary to a different portion of the target.

15 Claims, No Drawings

METHOD AND KIT FOR PERFORMING NUCLEIC ACID HYBRIDIZATION ASSAYS

This is a continuation of U.S. application Ser. No. 08/136,446, filed Oct. 14, 1993, now abandoned, which, in turn, is a continuation of U.S. patent application Ser. No. 07/798,027, filed Nov. 20, 1991, now U.S. Pat. No. 5,273,882, issued Dec. 28, 1993, which in turn is a continuation of U.S. application Ser. No. 07/512,092, filed Apr. 11, 1990, now abandoned, which in turn is a continuation of U.S. application Ser. No. 07/170,173, filed Mar. 14, 1988, now abandoned which in turn is a continuation of U.S. application Ser No. 06/744,800, filed Jun. 13, 1985, now abandoned.

BACKGROUND

The present invention relates in general to methods and kits for performing nucleic acid hybridization assays and in particular to methods and kits for immobilizing a target nucleic acid on a solid support by employing a labelled nucleotide probe, a nucleotide probe attached to a first complexing agent, and a second complexing agent attached to a support.

One characteristic property of nucleic acid, which forms the heritable material of all living organisms, is its ability to form sequence-specific hydrogen bonds with a nucleic acid having a complementary sequence of nucleotides. This ability of nucleic acids to form sequence-specific hydrogen bonds (i.e., to hybridize) with complementary strands of nucleic acid has been exploited in techniques generally called hybridization assays.

In a hybridization assay, a nucleic acid having a known sequence is used as a probe to search a sample for a "target" complementary sequence. Labelling of the hybrid formed by the probe and the target permits the detection and quantitation of complementary sequence in the sample.

Because all strains of a particular microorganism share a genetic component in the form of nucleic acids susceptible to diagnosis by means of a hybridization assay, such hybridization assays are valuable research and medical tools. Detection of specific target nucleic acids enables accurate diagnosis of bacterial, fungal and viral disease states in humans, animals and plants. Additionally, the ability to probe for a specific nucleotide sequence is of potential use in the identification and diagnosis of human genetic disorders.

One approach to labelling the probe for detecting a hybrid involves binding a radioisotope (e.g. $^{32}P$ or $^{125}I$) to the probe.

Non-radioactive labelling systems are also available. A first type employs a label which may be directly and covalently attached to the probe, such as fluorescent or chemiluminescent molecules (e.g., fluorescein or acridinium). A second type has a portion which is covalently attached to the DNA probe and non-covalently attached to labelled macromolecules.

An example of the second type of non-radioactive labelling system involves a biotin molecule which is covalently attached to a DNA probe and which forms a complex with fluorescent- or chemiluminescent-"labelled" avidin (or avidin derivatives such as streptavidin). Another example of the second type of non-radioactive labelling system is an antigen-"labelled" DNA probe which forms a complex with a fluorescent- or chemiluminescent-labelled antibody.

In the second type of labelling system, a probe is "labelled" with a reporter group to enable detection. A reporter is an agent which is used to associate a signal with a probe for indicating the presence or location of the probe. The signal itself., which is directly perceptible, may be generated by a separate or separable signal molecule. A label is properly a type of reporter which incorporates a signal.

Signal amplification may be achieved for biotin- or antigen-labelled DNA probes via the respective formation of a complex with avidin or with antibodies which may in turn be either covalently or non-covalently associated with an enzyme. [Leafy, et al., Proc. Natl. Acad. Sci. (USA), 80:4045–4049 (1983). This reporter group may then be incubated with the appropriate enzymatic substrate to generate a detectable signal which indicates the presence of target in the hybridization complex.

One approach to the attachment of labels to probes is described in Ward, European Patent Application No. 63,879. Ward discloses the preparation of probes having a biotin reporter molecule covalently attached to a purine or a pyrimidine ring. Selected biotinylated purines and pyrimidines are then directly incorporated within the phosphodiester backbone of nucleic acids of the probe by enzymatic means. In order to demonstrate that biotin-labelled native (double-stranded) DNA may be recognized by avidin, streptavidin or biotin-specific antibodies, Ward, et al. employ affinity chromatography. A complementary strand of DNA is synthesized on a single strand of DNA by a DNA polymerase from biotin- or iminobiotin-labelled purines or pyrimidines. The resulting, labelled, double-stranded DNA is selectively retained on an avidin- or a streptavidin-sepharose affinity column, as compared to non-labelled DNA. Ward, supra, at pages 24–26.

A biotin-labelled nucleic acid is employed in one approach to in situ hybridization in which biotin-labelled RNA is hybridized with denatured DNA in a chromosome squash. Polymethacrylate spheres are covalently attached to avidin which in turn binds to the biotin, thereby labelling portions of the DNA hybridized with the RNA. Manning, et al., Chromosoma (Berl.), 53:107–117 (1975). In addition, avidin-coated, polymethacrylate spheres have been employed in affinity chromatography to isolate biotin-labelled strands of DNA carrying a particular gene. Manning, et al., Biochemistry, 16:1364–1370 (1977).

In another approach to labelling for in situ hybridization, advantage is taken of the naturally-occurring bond between ribosomal protein and a pseudoribosomal gene in Drosophila. Antibodies are raised against the ribosomal protein and attached to polymethacrylate spheres which serve as labels for electron microscopy. Chooi, et al., Mol. Gen. Genet., 182:245–251 (1981).

The formation of a complex between an antigenic substance being assayed and one or more antibodies is also the basis for another type of biological detection technique called an immunoassay. Antibodies are white blood cell-produced proteins which are capable of combining with an antigen in a reaction which is specific for that antigen. Both antigens and antibodies may be referred to as immunological agents. An antibody only combines with certain portions (antigenic determinants) of the surface of the antigen, so that the antibody is specific to the degree that the determinant with which it combines is not also found on other antigens. At least one member of the antigen/antibody complex may be coupled to a signal molecule which permits detection, quantitative analysis on separation of the antigen/antibody complex from uncomplexed labelled antigen or antibody and other constituents of the sample. Antibodies of any type may be employed in immunoassays including polyclonal antibodies, a mixture of antibodies directed to different antigenic determinants, and monoclonal antibodies, antibodies directed to a single antigenic determinant.

Both immunoassays and hybridization techniques are employed in two-site or "sandwich" assays. In sandwich assays a target substance having the ability to form hybrid or immune complexes at two different places on the target at one time is detected.

Typically, a sandwich immunoassay involves coupling a monoclonal antibody directed to a first antigenic determinant to a solid support and exposing the support-coupled antibody to a sample containing a substance bearing the first and a second antigenic determinant. This results in the removal of the antigenic substance from the sample by the formation of a primary antibody-antigen complex which is bound to the support. Subsequent exposure of this complex to a second, labelled monoclonal antibody directed toward a second antigenic determinant on the antigenic substance creates an antibody-antigen-antibody sandwich which may be separated from the sample solution and measured. [See, e.g., David, et al., U.S. Pat. No. 4,376,110].

Sandwich hybridization assays include a two-step assay and a one-step assay. A two-step sandwich hybridization procedure involves the use of an immobilized target nucleic acid which is exposed in a first step to a first nucleic acid probe having a first portion complementary to the target and having a second portion which is not complementary to the target. In a second step, a second, labelled nucleic acid probe which is complementary to the second portion of the first probe is allowed to hybridize to the first probe, forming a "sandwich" with the first probe between the target and the second probe. Dunn, et al., Cell, 12:23–36 (1977). The sandwich hybridization procedure is relatively easy to perform and is not seriously affected by protein or other biological contaminants. Ranki, et al., Gene, 21:77–85 (1983). However, a two-step sandwich hybridization assay involves considerable delay associated with immobilization of the sample on a filter.

A one-step sandwich assay involves the use of a first nucleic acid probe immobilized on a filter. This first nucleic acid probe is complementary to a first portion of a target nucleic acid. In one step, the filter-bound first probe is exposed to a sample to be searched for the target nucleic acid sequence and to a second, labelled nucleic acid probe complementary to a second portion of the target nucleic acid, which portion is separate from (i.e., non-overlapping with) the portion of the target to which the first probe is complementary. Ranki, et al., U.S. Pat. No. 4,486,539. This one-step technique eliminates the delay caused by immobilization of a sample on a filter; eliminates differences between the types of treatment required for binding ribonucleic acid (RNA) and deoxyribonucleic acid (DNA) to certain types of support inasmuch as the first probe may be selected to suit the support; and is even less sensitive to contaminating materials in the sample, e.g., mucus, than is a direct hybridization assay where the target is bound to the support. Ranki, et al., Curr. Top. Microbiol. Immunol., 104:307–318 (1983). Nevertheless, leakage of the first probe from the support during hybridization occurs frequently and drastically diminishes the sensitivity of the assay.

Although both immunoassays and hybridization diagnostics are more rapid than conventional tests which require viable organisms and two to three days' culture, the antigens produced in a particular disease may vary from patient to patient and from one strain of a bacterium to another or from one strain of a virus to another, so that immunological diagnosis may be difficult. On the other hand, all strains of a bacterium or of a virus share a genetic component in the form of nucleic acids susceptible to diagnosis through the use of a nucleic acid probe.

Nevertheless, it is neither easy nor convenient to attach a single-stranded nucleic acid probe directly to a solid support for use in a sandwich hybridization assay. For example, the attachment of a nucleic acid to a nitrocellulose sheet involves fixing the nucleic acid by contact with the sheet for 12–15 hours and baking the nucleic acid onto the sheet for two hours. See, e.g., Thomas, Proc. Natl. Acad. Sci. (USA), 77:5201 (1980). Such preparation of a DNA-coated nitrocellulose sheet may easily consume as much as a full working day, a factor which limits the clinical usefulness of nucleic acid hybridization.

Furthermore, because the nucleic acid probe is sequence-specific for a particular target molecule, the procedure for attaching the probe to the support must be performed for each target molecule to be detected. Thus, in order to detect a number of different DNA sequences, a diagnostic laboratory must prepare an equal number of types of supports.

In addition, it generally takes longer to hybridize complementary strands of nucleic acid than it does, for example, to form an immunological complex between an antigen and an antibody. Hybridization itself is much more quickly accomplished in solution than it is where one of the complementary sequences is attached to a solid support.

Affinity chromatographic techniques may be employed to isolate and purify nucleic acids [see, e.g., Inouye, et al., J. Biol. Chem., 23:8125–8129 (1973)] or tRNA [Miller, et al., Biochim. Biophys. Acta, 366:188–198 (1974)] or tRNA cistrons [Salomon, et al., Biochemistry, 14:4046–4050 (1975)]. However, these techniques rely upon the difficult step of forming antibodies to specific bases in a nucleic acid (Inouye, et al., supra; Salomon, et al., supra) or upon the use of a derivatized, naturally-occurring ribonucleic acid (tRNA) (Miller, et al., supra) and are thus not readily applied in general to hybridization assays.

Thus, there exists a continuing interest and need in the art for easy, convenient and rapid nucleic acid hybridization "sandwich" assays capable of accurately detecting target molecules in a sample.

BRIEF SUMMARY

A method according to the present invention for the isolation and quantitative detection of a selected target nucleic acid sequence from solution involves hybridizing the target nucleic acid sequence in solution to a first single-stranded nucleic acid probe which has a sequence complementary to a selected portion of the target sequence and which is therefore capable of hybridizing therewith. The first probe sequence is covalently attached to a first complexing agent. A second single-stranded nucleic acid probe, which has a sequence complementary to a different selected portion of the target sequence than that which is complementary to the first probe, hybridizes to the target. A detectable reporter group is attached to the second probe sequence.

Following solution hybridization, the method according to the present invention further involves immobilizing the hybrid sequence by adding to the hybridization solution a second complexing agent bound to a solid support capable of binding to the first complexing agent on the first probe. There is thus obtained a sandwich comprising the second complexing agent-support, complexed with the first complexing agent-first probe hybridized to the target, in turn hybridized to the second probe. An assay is then performed to detect and quanitate the bound reporter.

A kit according to the present invention is used for performing a hybridization assay on a sample containing a selected target nucleic acid sequence from solution. In this kit a first probe has a nucleic acid sequence complementary to a first portion of the target nucleic acid sequence and is attached to a first complexing agent. A second single-stranded nucleic acid probe associated with the first nucleic acid probe has a nucleic acid sequence complementary to a second portion of the target sequence and is associated with the first probe. A reporter group is attached to the second nucleic acid probe. A solid support, also associated with the first nucleic acid probe, is attached to a second complexing agent which has a first complexing agent-binding portion.

Another method according to the present invention increases the capture efficiency associated with immobilizing a target nucleic acid sequence on a solid support. This method involves exposing the target nucleic acid sequence to at least two first probes, each having a nucleic acid sequence complementary to a different portion of the target nucleic acid sequence and each having a support-binding portion. In solution, the target nucleic acid sequence is hybridized to at least one of the first probes. The support-binding portion of the at least one of the first probes attaches to a first probe-binding portion on a solid support.

Another kit according to the present invention is useful for performing a hybridization assay on a sample containing a target nucleic acid sequence. The kit includes at least two first probes, each of which has a nucleic acid sequence complementary to a different portion of the target nucleic acid sequence. A second probe is associated with the first probes. The second probe has a sequence which is complementary to a portion of the target nucleic acid sequence that is separate from any portion complementary to any first probe. The second probe is also attached to a reporter group. A solid support is also associated with the first probes and has a first probe-binding portion.

Other aspects and advantages of the present invention will become apparent to those skilled in the art upon consideration of the following detailed description.

DETAILED DESCRIPTION

In a preferred embodiment of the method according to the present invention, a target nucleic acid sequence in solution may be detected or quantified by measuring the amount of a signal associated with an immobilized "sandwich" hybrid by conventional methods. The method is also useful in separating a hybridized target sequence from a solution where detection is not required. The method according to the present invention may be employed where the target oligonucleotide sequence is a deoxyribonucleic or ribonucleic acid sequence. In either case, depending on preference for a DNA-DNA, RNA-RNA, or DNA-RNA hybridization between the first probe, labelled second probe, and target, the probe sequences may be deoxyribonucleic or ribonucleic acid sequences.

The method is desirably employed on a double-stranded target sequence when the double-stranded sequence is denatured prior to use in the hybridization and is also useful for detection of single-stranded target sequences. The target sequence employed in this method may be of any length but preferably greater than about 20 residues in length.

The first probe sequence itself may be any nucleic acid sequence capable of covalently binding to the selected first complexing agent and having at least a portion designed to complement and to stably hybridize with a portion of the target sequence. The first complexing agent, which is covalently attached to the first probe, may be an antigen, such as fluorescein or an antibody, such as anti-fluorescein; or may be biotin or avidin; or may be a lectin, such as concanavalin A or a carbohydrate having, for example, a-glucosyl residues or a-mannosyl residues specific for concanavalin A.

A lectin is a protein which has combining groups that react with specific carbohydrate components of another molecule to form a complex in a fashion similar to the interaction of an antibody with an antigen. Biotin, a vitamin, is an imidazole derivative which combines with avidin, a protein found in eggwhite, to form a biotin-avidin complex. Thus antigens and the antibodies which bind to them, lectins and the cabohydrate components to which they bind, and biotin and avidin, all may be distinguished as complexing agents, forming non-covalent bonds, from nucleic acids which are sequence-specific hybridizing agents, forming hydrogen bonds.

Several techniques may be employed to generate single-stranded polynucleotide probes for use in hybrization. A probe sequence complementary to a desired "target" sequence may be obtained: as a messenger RNA sequence corresponding to a target sequence; or complementary DNA obtained from reverse transcription of messenger RNA by the enzyme reverse transcriptase; or as genomic DNA obtained from the target genome by endonuclease digestion.

A probe sequence may be "amplified" by insertion into a DNA plasmid, such as pBR322, which will replicate in a bacterial host cell. Plasmid DNA is double-stranded and may be labelled by well-known nick translation procedures.

Alternatively, a probe sequence may be amplified by inserting the desired sequence into a single-stranded virus, such as the bacteriophage M13. The virus containing the probe sequence thereafter infects the bacterial culture and multiplies, making billions of copies of the probe sequence attached to viral DNA. The viral clone DNA may be isolated as either single-stranded or double-stranded DNA. Double-stranded viral DNA may be labelled by nick translation. Single-stranded viral DNA may be rendered detectable through use of primed synthesis of complementary strand DNA using labelled nucleotides according to the procedures of Hu, et al., *Gene*, 17:271–277 (1982). See Ranki, et al., *Gene*, 21:77–85 (1983), which relates to M13 and pBR322 amplification systems for generating single-stranded probes for use in sandwich hybridization assays.

Like the first probe, the second probe may have any nucleic acid sequence which is different than that of the first probe and which is designed to complement and hybridize with the target at a portion of the target separate from (i.e., not overlapping) the portion to which the first probe hybridizes.

A reporter group may be covalently attached to the second probe. The reporter group may be a radioisotopic label, such as $^{125}I$, $^{32}P$, or the like Alternatively, chelating moieties, such as ethylene diamine tetraacetic acid (EDTA) or diethyltriamino pentacetic acid (DTPA), may be employed to attach heavy metal labels to the probe. Appropriate heavy metal labels include $^{57}Co$, $^{63}Ni$, $^{111}In$, $^{99}Tc$, $^{55}Fe$, $^{51}Cr$, and the like. Non-isotopic labels, e.g., fluorescent compounds and chemiluminescent compounds, may also be employed in the method according to the present invention. Non-radioactive reporter groups which may be attached to the second probe include the enzyme alkaline phosphatase linked, for example, by biotin or avidin, to the second probe. Incubation in a solution of a methylumberliferone phosphate substrate results in fluorescence produced by the action of the enzyme on the substrate.

Any solid support to which a complexing agent may be bound is useful in this method, including both porous and non-porous, polymeric and non-polymeric supports. Examples of a solid support suitable for use in the method include silicates in general and glass, silica gel, and controlled pore glass in particular; cellulose and nitrocellulose paper; polystyrene; latex and rubbers; and fluorocarbon resins, such as Teflon® and the like.

The second complexing agent bound to the support may be any agent which forms a complex with the first complexing agent on the first probe. For example, the second complexing agent may be an antibody (e.g., IgG, IgM, or IgA), including a monoclonal antibody such as anti-fluorescein antibody where the antigen on the first probe is fluorescein.

As is clear to one skilled in the art, the present invention provides several advantages over the conventional attachment of a first nucleic acid probe to a solid support. Because a single combination of first and second immunological agents may be used with a wide variety of probe and target sequences, the present invention eliminates the need for a laboratory to prepare a support specific to each sequence to be detected. Furthermore, to the extent that hybridization according to the present invention occurs between complementary strands in solution rather than between one in solution and another on a solid support, the hybridization procedure proceeds more quickly. Furthermore, complex formation is much more rapid than hybridization so that the use of complex formation rather than hybridization to attach the target to a support reduces assay time even further. Also, attachment of antibodies, antigens, lectine, carbohydrates, biofin oravidin to a solid support does not require as many steps and is not as time-consuming as is the attachment of a sequence of nucleic acid to a solid support. Cf., e.g., Thomas, Proc. Natl. Acad. Sci. (USA), 77:5201–5205 (1980).

Thus, the present invention provides the means for accomplishing hybridization diagnostic tests much more easily, rapidly, and conveniently.

The following examples illustrate the practice of the method of the present invention. Specifically demonstrated are hybridization assays employing the two-probe system to detect and quantitate the amount of desired target sequence in a solution.

For use in the solution hybridization procedures of the following examples, a single-stranded phage containing either the (+) plus (coding) strand or the (−) minus (anticoding) strand of Herpes Simplex Virus Type I (HSV-I) glycoprotein D (gD) gene was employed as the target sequence. A portion of the double-stranded gene sequence is set out in Table I below, the bottom strand being the anticoding strand. This sequence has been published in Watson, et al., Science, 218:381–384 (1982). Portions of the plus and minus strands have been employed as probes according to the present invention. These single-stranded probe sequences have been designated on Table I by a lettered line drawn above the coding strand of the gene, or by a lettered and numbered line drawn below the anticoding strand of the gene.

TABLE I

```
              10              20              30              40
     .        .       .       .       .       .       .       .
GTG GCC CCG GCC CCC AAC AAA AAT CAC GGT AGC CCG GCC GTG
TAC CGG GGC CGG GGG TTG TTT TTA GTG CCA TCG GGC CGG CAC 50              60              70              80
     .        .       .       .       .       .       .       .
TGA CAC TAT CGT CCA TAC CGA CCA CAC CGA CGA ACC CCT AAG
ACT GTG ATA GCA GGT ATG GCT GGT GTG GCT GCT TGG GGA TTC 90             100             110             120
     .        .       .       .       .       .       .       .
GGG GAG GGG CCA TTT TAC GAG GAG GAG GGG TAT AAC AAA GTC
CCC CTC CCC GGT AAA ATG CTC CTC CTC CCC ATA TTG TTT CAG 130             140             150             160
     .        .       .       .       .       .       .       .
TGT CTT TAA AAA GCA GGG GTT AGG GAG TTG TTC GGT CAT AAG
ACA GAA ATT TTT CGT CCC CAA TCC CTC AAC AAG CCA GTA TTC 170            180             190             200            210
     .        .       .       .       .       .       .       .
CTT CAG CGC GAA CGA CCA ACT ACC CCG ATC ATC AGT TAT CCT
GAA GTC GCG CTT GCT GGT TGA TGG GGC TAG TAG TCA ATA GGA
                         R-1

220             230             240             250
     .        .       .       .       .       .       .       .
TAA GGT CTC TTT TGT GTG GTG CGT TCC GGT ATG GGG GGG ACT
ATT CCA GAG AAA ACA CAC CAC GCA AGG CCA TAC CCC CCC TGA 260             270             280             290
     .        .       .       .       .       .       .       .
GCC GCC AGG TTG GGG GCC GTG ATT TTG TTT GTC GTC ATA GTG
CGG CGG TCC AAC CCC CGG CAC TAA AAC AAA CAG CAG TAT CAC 300             310    A        320             330
     .        .       .       .       .       .       .       .
GGC CTC CAT GGG GTC CGC GGC AAA TAT GCC TTG GCG GAT GCC
CCG GAG GTA CCC CAG GCG CCG TTT ATA CGG AAC CGC CTA CGG
```

TABLE I-continued

```
      340             350             360            370       B
TCT CTC AAG ATG GCC GAC CCC AAT CGC TTT CGC GGC AAA GAC
AGA GAG TTC TAC CGG CTG GGG TTA GCG AAA GCG CCG TTT CTG 380           390             400            410           420
CTT CCG GTC CTG GAC CAG CTG ACC GAC CCT CCG GGG GTC CGG
GAA GGC CAG GAC CTG GTC GAC TGG CTG GGA GGC CCC CAG GCC
                                A-1

430       C   440             450             460
CGC GTG TAC CAC ATC CAG GCG GGC CTA CCG GAC CCG TTC CAG
GCG CAC ATG GTG TAG GTC CGC CCG GAT GGC CTG GGC AAG GTC 470           480             490     D     500
CCC CCC AGC CTC CCG ATC ACG GTT TAC TAC GCC GTG TTG GAG
GGG GGG TCG GAG GGC TAG TGC CAA ATG ATG CGG CAC AAC CTC
              B-1

510             520             530             540
CGC GCC TGC CGC AGC GTG CTC CTA AAC GCA CCG TCG GAG GCC
GCG CGG ACG GCG TCG CAC GAG GAT TTG CGT GGC AGC CTC CGG
                        C-1

550     E   560             570             580
CCC CAG ATT GTC CGC GGG GCC TCC GAA GAC GTC CGG AAA CAA
GGG GTC TAA CAG GCG CCC CGG AGG CTT CTG CAG GCC TTT GTT
                                                D-1

590           600             610           620           630
CCC TAC AAC CTG ACC ATC GCT TGG TTT CGG ATG GGA GGC AAC
GGG ATG TTG GAC TGG TAG CGA ACC AAA GCC TAC CCT CCG TTG 640             650             660           670
TGT GCT ATC CCC ATC ACG GTC ATG GAG TAC ACC GAA TGC TCC
ACA CGA TAG GGG TAG TGC CAG TAC CTC ATG TGG CTT ACG AGG
              E-1

G   680             690             700             710
TAC AAC AAG TCT CTG GGG GCC TGT CCC ATC CGA ACG CAG CCC
ATG TTG TTC AGA GAC CCC CGG ACA GGG TAG GCT TGC GTC GGG
                                    F-1

720             730             740             750
CGC TGG AAC TAC TAT GAC AGC TTC AGC GCC GTC AGC GAG GAT
GCG ACC TTG ATG ATA CTG TCG AAG TCG CGG CAG TCG CTC CTA
                  G-3

760             770             780           790     I
AAC CTG GGG TTC CTG ATG CAC GCC CCC GCG TTT GAG ACC GCC
TTG GAC CCC AAG GAC TAC GTG CGG GGG CGC AAA CTC TGG CGG
                      G-1

800           810             820             830           840
GGC ACG TAC CTG CGG CTC GTG AAG ATA AAC GAC TGG ACG GAG
CCG TGC ATG GAC GCC GAG CAC TTC TAT TTG CTG ACC TGC CTC
                                        H-1

850     J   860             870             880
ATT ACA CAG TTT ATC CTG GAG CAC CGA GCC AAG GGC TCC TGT
TAA TGT GTC AAA TAG GAC CTC GTG GCT CGG TTC CCG AGG ACA 890             900             910           920
AAG TAC GCC CTC CCG CTG CGC ATC CCC CCG TCA GCC TGC CTC
TTC ATG CGG GAG GGC GAC GCG TAG GGG GGC AGT CGG ACG GAG
              I-1
```

TABLE I-continued

```
          930              940              950              960
TCC CCC CAG GCC TAC CAG CAG GGG GTG ACG GTG GAC AGC ATC
AGG GGG GTC CGG ATG GTC GTC CCC CAC TGC CAC CTG TCG TAG
         J-3                    J-1

970              980              990             1000
GGG ATG CTG CCC CGC TTC ATC CCC GAG AAC CAG CGC ACC GTC
CCC TAC GAC GGG GCG AAG TAG GGG CTC TTG GTC GCG TGG CAG
                                             K-1

1010            1020             1030            1040         1050
GCC GTA TAC AGC TTG AAG ATC GCC GGG TGG CAC GGG CCC AAG
CGG CAT ATG TCG AAC TTC TAG CGG CCC ACC GTG CCC GGG TTC 1060              1070           1080              1090
GCC CCA TAC ACG AGC ACC CTG CTG CCC CCG GAG CTG TCC GAG
CGG GGT ATG TGC TCG TGG GAC GAC GGG GGC CTC GAC AGG CTC
                       L-1

1100              1110           1120              1130
ACC CCC AAC GCC ACG CAG CCA GAA CTC GCC CCG GAA GAC CCC
TGG GGG TTG CGG TGC GTC GGT CTT GAG CGG GGC CTT CTG GGG
                                      M-1

1140              1150           1160              1170
GAG GAT TCG GCC CTC TTG GAG GAC CCC GTG GGG ACG GTG GCG
CTC CTA AGC CGG GAG AAC CTC CTG GGG CAC CCC TGC CAC CGC 1180              1190           1200              1210
CCG CAA ATC CCA CCA AAC TGG CAC ATC CCG TCG ATC CAG GAC
GGC GTT TAG GGT GGT TTG ACC GTG TAG GGC AGC TAG GTC CTG
        N-1                                      O-1

1220            1230             1240            1250         1260
GCC GCG ACG CCT TAC CAT CCC CCG GCC ACC CCG AAC AAC ATG
CGG CGC TGC GGA ATG GTA GGG GGC CGG TGG GGC TTG TTG TAC
                                   P-1

1270              1280           1290              1300
GGC CTG ATC GCC GGC GCG GTG GGC GGC AGT CTC CTG GCA GCC
CCG GAC TAG CGG CCG CGC CAC CCG CCG TCA GAG GAC CGT CGG 1310              1320           1330              1340
CTG GTC ATT TGC GGA ATT GTG TAC TGG ATG CAC CGC CGC ACT
GAC CAG TAA ACG CCT TAA CAC ATG ACC TAC GTG GCG GCG TGA 1350            1360             1370            1380
CGG AAA GCC CCA AAG CGC ATA CGC CTC CCC CAC ATC CGG GAA
GCC TTT CGG GGT TTC GCG TAT GCG GAG GGG GTG TAG GCC CTT
                     Q-1

1390             1400             1410            1420
GAC GAC CAG CCG TCC TCG CAC CAG CCC TTG TTT TAC TAG ATA
CTG CTG GTC GGC AGG AGC GTG GTC GGG AAC AAA ATG ATC TAT
                                             S-1

1430            1440             1450            1460         1470
CCC CCC CTT AAT GGG TGC GGG GGG GTC AGG TCT GCG GGG TTG
GGG GGG GAA TTA CCC ACG CCC CCC CAG TCC AGA CGC CCC AAC 1480              1490           1500              1510
GGA TGG GAC CTT AAC TCC ATA TAA AGC GAG TCT GGA AGG GGG
CCT ACC CTG GAA TTG AGG TAT ATT TCG CTC AGA CCT TCC CCC 1520              1530           1540              1550
GAA AGG CGG ACA GTC GAT AAG TCG GTA GCG GGG GAC GCG CAC
CTT TCC GCC TGT CAG CTA TTC AGC CAT CGC CCC CTG CGC GTG
                                 T-1
```

TABLE I-continued

```
   1560           1570           1580           1590
CTG TTC CGC   CTG TCG CAC   CCA CAG CTT   TTT CGC GAA   CCG TCC
GAC AAG GCG   GAC AGC GTG   GGT GTC GAA   AAA GCG CTT   GGC AGG

1600
CGT TTT CGG GAT
GCA AAA GCC CTA
```

Three different targets are used in the examples. A first single-stranded phage target, phage 2 (Φ2), contains 1,360 bases of the HSV-I D (gD) gene (i.e., bases 167 through 1,526, initiation codon nucleotide number 241 cloned into a plasmid, M13mp18. The minus strand sequence of gD in Φ2 is employed as a target complementary to the (+) plus strand probes identified above. A second single-stranded phage target, NPE #1, contains the entire 2.9 kilobases of the HSV-I gD sequence and is cloned into M13mp18. The (+) plus strand sequence of gD in NPE #1 is cloned to provide a target complementary to the (−) minus probes identified above. Lastly, a double-stranded plasmid target, Bam HI-J, is a Bam HI restriction fragment of HSV-I which contains the entire 2.9 kilobases of the HSV-I gD sequence, along with 3.3 kilobases of surrounding HSV-I sequences. Bam HI-J was cloned into the plasmid pBR322 and this plasmid was used as a double-stranded target for mimicking hybridization to HSV-I virus. See Roizman, et al., *Curr. Top. Microbiol. Immunol.* 104:273 (1983).

The following examples describe a series of experiments demonstrating various aspects of the present invention.

Example 1 shows the ability of an antibody-coated support to capture a hybridization sandwich comprising two probes bound to a target. Example 2 illustrates the increase in capture efficiency obtained through the use of multiple antigen labelled probes. Example 3 demonstrates the effects of target concentration on the efficiency and sensitivity of the hybridization assay according to the present invention. Example 4 illustrates the utility of the present invention in detecting a radioactively-labelled hybridization sandwich. Example 5 shows the effectiveness of the present invention for detecting a non-radioactively-labelled hybridization sandwich. Example 6 illustrates the usefulness of the method according to the present invention in detecting the presence of a double-stranded DNA target.

EXAMPLE 1

The ability of an antibody-coated solid support to capture a hybridization sandwich formed by two probes and a target was tested. An oligonucleotide first probe was labelled with an antigen at its 5' end. A second probe was an oligonucleotide carrying a reporter group. A portion of the target was complementary to each probe.

Specifically, the first probe was oligonucleotide G as described above. Such 5' labelling of oligonucleotide G may be accomplished with fluorescein.

Oligonucleotide G was 5' fluorescein labelled by reacting a 5' amine functionalized oligonucleotide G with fluorescein isothiocyanate. The 5' amine functionalized oligonucleotide G was formed by reacting oligonucleotide G bound by its 3' end to a solid support with a phosphoramidite having the general formula $[(CH_3)_2CH]_2NP(OCH_3)O(CH_2)_8NH$ (DMT) wherein DMT is a dimethoxytrityl group.

In the synthesis of this phosphoramidite, about 8 ml of diazomethane-ether solution were added to 159.2 mg (1 mmole) of ω-aminocaprylic acid (available from Aldrich Chemical, Milwaukee, Wis.) in 10 ml of methanol. The methanol was evaporated to yield 174.9 mg of ω-aminocaprylic acid methyl ester. Next, 173 mg (1 mmole) of the ω-aminocaprylic acid methyl ester, 1 mmole of dimethoxytrityl chloride, and 1 mmole of diisopropylethyl amine were added to 5 ml of anhydrous tetrahydrofuran under an argon atmosphere at 0° C. This mixture was warmed to 25° C. and stirred for 1 hour. The solvent was evaporated and the crude product was diluted with 50 ml of ethyl acetate and washed successively with two portions of water, saturated bicarbonate, and brine. The product was dried over anhydrous magnesium sulfate and evaporated to yield 460 mg of a dimethoxytrityl derivative of the ω-aminocaprylic acid methyl ester (ACAM-DMT).

To 0.17 mmoles of ACAM-DMT in 1 ml of anhydrous tetrahydrofuran under an argon atmosphere at −78° C. was added 1.24 ml of I molar lithium aluminum hydride in tetrahydrofuran. This reaction mixture was stirred for 5 minutes at −78° C. and was then stirred for 30 minutes at 25° C. before being diluted with 10 ml of 5% $H_2O$ in tetrahydrofuran, 200 ml of ether, 3 g of cellite, and 0.5 g of anhydrous magnesium sulfate. The resulting mixture was stirred for 30 minutes and filtered to yield an alcohol having the general formula $HO(CH_2)_8NH$—DMT.

To 0.72 mmoles of $HO(CH_2)_8NH$—DMT in 10 ml of anhydrous dichloromethane was added 0.76 mmoles of diisopropyl ethyl amine and 0.76 mmoles of chloro-N,N'-diisopropylaminomethoxy phosphene (as available from American Bionuclear, Emeryville, Calif.). This mixture was stirred for 40 minutes at 25° C., and then diluted with 50 ml of ethyl acetate and washed with four portions of brine. The product of this reaction was the phosphoramidite used for labelling oligonucleotide G above.

The second probe was oligonucleotide A, which had been labelled with $^{32}P$ according to the procedure of Maniatis, et al., *Cell*, 15:687 (1978). The specific activity of the probe on the date of use was $3.2 \times 10^6$ cpm/pmole.

Oligonucleotide G without a 5' fluorescein label was used as a first probe control. A second control probe, having the sequence 5' CATGATCTTGCGGTCGGATTCTTC 3', which does not complement any of the target sequence, was also $^{32}P$-labelled and had a specific activity on the date of use of $3.2 \times 10^6$ cpm/picomole.

The target used was single-stranded Φ2. Single-stranded Φ2 is complementary to the first and second probes and to the first probe control, but not to the second control probe.

As a support, one-quarter-inch polystyrene beads of the sort available from Pierce Chemical, Rockland, Ill., were coated with fluorescein antibody (anti-fluorescein). Anti-fluorescein production was induced in rabbits. The anti-fluorescein was purified by ammonium sulfate precipitation, foil, owed by DEAE cellulose chromatography. In solution, the anti-fluorescein had an affinity of approximately $10^{12}$ and quenched the fluorescence of fluorescein by about 99%.

To prepare an anti-fluorescein-coated bead, the bead is cleaned by ultrasonication for 15 seconds in 10 mM NaHCO$_3$ buffer at pH 8. After ultrasonication, the beads are washed in deionized water until all fines are removed. Approximately 200 beads are covered by 40 ml of 10 mM NaHCO$_3$. Next, 7 ml of purified anti-fluorescein at a concentration of 0.57 mg/ml is added. The beads are incubated for approximately 65 hours at room temperature. After incubation, the beads are washed with deionized water and air-dried on a suction filter.

Each of the anti-fluorescein-coated beads is capable of binding approximately 1 pmole of fluorescein, as demonstrated by incubation of single beads with 1.5 ml of 1 nM fluorescein in TDX buffer (0.1M NaPO$_4$, pH 7.5; 0.1% NAN$_3$; 0.1% bovine gammaglobulin). During 20 hours of incubation at 25° C., 97% of the fluorescein was removed from solution. After washing the beads three times in 5 ml of deionized water and blotting the beads dry after each wash, the beads were incubated in 0.1M NaOH for 10 minutes, in which 60% of the originally applied amount of fluorescein was released into solution. Thus, each bead has approximately 0.9 pmole of fluorescein binding capacity.

(1) A series of capture experiments employing 5'-fluorescein-labelled oligonucleotides, 5'-biotin-labelled oligonucleotides (both 3'-$^{32}$P end-labelled), and kinased $^{32}$P-labelled oligonucleotides and polystyrene beads coated with anti-fluorescein were run under the following conditions.

With 200 µg/ml denatured sheared salmon sperm DNA (Sigma Chemical Company, St. Louis, Mo.) containing picomole of one of the $^{32}$P-labelled oligonucleotides, 100 µl of TDX buffer (0.1M sodium phosphate, pH 7.5; 0.1% NAN$_3$; and 0.01% bovine gamma globulin, Sigma Chemical Company, St. Louis, Mo.) was mixed. An anti-fluorescein-coated polystyrene bead was added to this solution. After incubating this system for 18 hours at 25° C., the bead was removed and washed for 5 minutes in 1 ml of TDX buffer at 25° C. The bead was then counted in a scintillation counter.

The stability of the antibody complex on the bead was tested by washing the bead for 5 minutes at increasing temperatures. The capture efficiency and stability of a series of such beads is shown in Table II.

TABLE II

| Temperature | Percent cpm Capture | | |
|---|---|---|---|
| | Complexes | | |
| | 5' fluorescein-labelled complex | 5' biotin-labelled complex | 5' $^{32}$P-labelled complex |
| 25 | 63 | 4 | 3 |
| 35 | 61 | 1 | 0 |
| 45 | 56 | 0 | 0 |
| 55 | 51 | 0 | 0 |
| 65 | 42 | 0 | 0 |
| 75 | 35 | 0 | 0 |
| 85 | 20 | 0 | 0 |
| 95 | 0 | 0 | 0 |

As illustrated by Table II, these beads have a high capture efficiency and stability of the sort which is useful in a hybridization capture system. Because little or no biotin or $^{32}$P-labelled oligonucleotide binds to these beads, indicating little non-specific binding to the beads, the background in such a system is very low.

(2) In order to more precisely determine the rate capture of a fluorescein-labelled oligonucleotide by a fluorescein antibody-coated bead, each of a series of beads was incubated for a different amount of time with picomole of 5'-fluorescein-labelled oligonucleotide A which had been 3' end-labelled with $^{32}$P. The percent of capture was determined for each bead and the results are shown below in Table III.

TABLE III

| Time | Percent Oligonucleotide Capture |
|---|---|
| 0 | 0 |
| 15 minutes | 20 |
| 30 minutes | 45 |
| 1 hour | 48 |
| 2 hours | 75 |
| 3 hours | 91 |
| 4 hours | 90 |
| 5 hours | 88 |
| 6 hours | 86 |
| 7 hours | 85 |
| 8 hours | 82 |
| . | |
| . | |
| 20 hours | 68 |

As illustrated in Table III, 90% of the 5' fluorescein-labelled oligonucleotide is captured by the bead in 2 to 3 hours. The slow decline in the amount of radiolabel over time on the bead most likely represents a small amount of leakage of the antibody from the bead.

(3) Experiment 1. The capture-efficiency of the anti-fluorescein-coated beads being established, 1 picomole of the first probe (5'-fluorescein-labelled oligonucleotide G), 1 picomole of the second probe ($^{32}$P-labelled oligonucleotide A), specific activity on date of use 3.2×10$^6$ cpm/picomole), and 1 picomole of the target (Φ2 SS, complementary to both the first and second probes) were diluted to 50 µl with 5 X SSPE diluted from 20 X SSPE (3.6M NaCl; 0.23M NaH$_2$PO$_4$, pH 7.5; and 20 mM EDTA). This hybridization solution was incubated for 3 hours at 50° C. This hybridization solution was diluted with 100 µl of TDM buffer and one anti-fluorescein-coated bead was added. After incubation for 3 hours at 25° C., the bead was washed with 1 ml of TDX buffer for 5 minutes at 37° C. and was re-washed with 1 ml of TDX buffer for 5 minutes at 37° C. before counting in a scintillation counter.

Control Experiments. Three control experiments were run according to the same protocol but with the following modifications. In a first control experiment (Control 1), 5' fluorescein-labelled oligonucleotide G, as a first probe, and 5' $^{32}$P-labelled oligonucleotide A, as a second probe, were incubated with the anti-fluorescein-coated bead in the absence of any target. A second control experiment (Control 2) involved the use of 1 picomole of unlabelled oligonucleotide G as a first probe for the fluorescein-labelled oligonucleotide G of experiment 1. Finally, a third control experiment (Control 3) was performed with 1 picomole of 5'-fluorescein-labelled oligonucleotide G, as a first probe, 1 picomole of a $^{32}$P-labelled oligonucleotide designated $^{32}$-B$_2$ (the sequence of which is not complementary to Φ2 SS), as a second probe, and 1 picomole of Φ2 SS as a target.

The results of these experiments are summarized in Table IV.

TABLE IV

| Experiment | % $^{32}$P Oligonucleotide Bound to the Bead |
|---|---|
| Experiment 1 | 4.2 |
| Control 1 | 0.002 |
| Control 2 | 0.07 |
| Control 3 | 0.22 |

A comparison of Experiment 1 and Control 1 indicates that the hybrid comprising fluorescein-labelled oligonucleotide G, Φ2 SS, and $^{32}$P-labelled oligonucleotide A may be selectively captured by an anti-fluorescein-coated solid support. Controls 2 and 3 demonstrate that in the absence of the correct antigen-labelled first probe or in the absence of the correct target complementary second probe, a hybrid is not effectively generated or captured.

EXAMPLE 2

In an attempt to increase the capture efficiency of the hybridization assay according to the present invention, several fluorescein-labelled oligonucleotide probes were simultaneously introduced into the hybridization solution. Four experiments were run under identical reaction conditions.

A total of 250 femtomoles of fluorescein-labelled oligonucleotide was used in each experiment. In Experiment 1, 250 femtomoles of a single fluorescein-labelled oligonucleotide were used. The hybridization solution of Experiment 2 contained 125 femtomoles of each of two different fluorescein-labelled oligonucleotides, while Experiment 3 involved 83 femtomoles of each of three different fluorescein-labelled oligonucleotides in the hybridization solution. In Experiment 4, the hybridization solution contained 28 femtomoles of each of nine different fluorescein-labelled oligonucleotides.

Specifically, in Experiment 1, a 5 X SSPE solution of 250 femtomoles of 5' fluorescein-labelled oligonucleotide B, 25 femtomoles of a target Φ2 SS and 100 femtomoles of $^{32}$P-labelled oligonucleotide A was boiled for 5 minutes to denature any double-stranded secondary structure which might be present and incubated at 50° C. for 3 hours. The hybridization solution was diluted with 50 μl of 5 X SSPE before adding one anti-fluorescein-coated bead. The bead was incubated in this solution for 4 hours at 25° C. and was washed in 1 ml of 5 X SSPE for 5 minutes at 25° C. before counting in a scintillation counter.

Experiment 2 duplicated the conditions of Experiment 1 except for the substitution of 125 femtomoles of each of 5' fluorescein-labelled oligonucleotides J and D in the place of the 250 femtomoles of 5' fluorescein-labelled oligonucleotide B.

In Experiment 3, the conditions of Experiment 1 were duplicated except for the substitution of 83 femtomoles of each of the 5' fluorescein-labelled oligonucleotides J, G, and D for the 250 femtomoles of 5' fluorescein-labelled oligonucleotide B of Experiment 1.

In Experiment 4, the conditions of Experiment 1 were duplicated except for the substitution of 28 femtomoles of each of the 5' fluorescein-labelled oligonucleotides B, C, D, E, F, G, H, I, and J for the 250 femtomoles of 5' fluorescein-labelled oligonucleotide B of Experiment 1.

The results of these four experiments are summarized in Table V, wherein the percentage of sandwich hybridization complex captured by the bead is expressed as the ratio of $^{32}$P oligonucleotide A captured per total amount of target present.

TABLE V

| Experiment | Percentage of Complex Captured |
|---|---|
| 1 | 5.4 |
| 2 | 14.2 |
| 3 | 21.4 |
| 4 | 61.2 |

As indicated in Table V, a roughly linear increase in hybridization efficiency was observed with increasing the number of different probes used. A 60% capture efficiency was achieved when all nine fluorescein oligonucleotides were used.

In general, the greater the number of points of stringency within a system, the less likely becomes the detection of false positives. In a conventional hybridization sandwich assay, the use of a separate probe for each of labelling and immobilization provides an additional point of stringency over use of a single probe for both purposes in that detection of a target sequence requires the occurrence of two independent events, i.e., the hybridization of both probes to the target. Consequently, it is believed that by the use of several first probes, the points of stringency are multiplied linearly, so that the efficiency of detection of a particular target sequence is increased relatively to the efficiency of detection of an incorrect sequence. Similarly, the use of a non-hybridization reaction to attach the first probe to the support serves to minimize detection of false positives by introducing a point of stringency associated with an antibody/antigen interaction into a system which already has a nucleic acid-related point of stringency and which would otherwise have only another nucleic acid-related point of stringency in its place.

In the following example, the linearity of the capture efficiency of a hybridization complex over a range of target concentrations (10 femtomoles to 16 attomoles) was investigated in two sets of experiments.

EXAMPLE 3

In order to determine the effect of target concentration on the efficiency and sensitivity of the immuno-hybridization assay according to the present invention when run in the presence of extraneous DNA, the concentration of a target was varied from 10 femtomoles to 16 attomoles.

In each of six hybridization reactions, a solution of 111 femtomoles of each of 5' fluorescein-labelled oligonucleotides B, C, D, E, F, G, H, I, and J; 10 μg of human placental DNA (available from Sigma Chemical Company, St. Louis, Mo.); and 100 femtomoles of $^{32}$P-labelled oligonucleotide A in 5 X SSPE was prepared. To this basic solution, a varying amount of Φ2 SS target was added. In Experiment 1, 10 femtomoles of target was added. In Experiment 2, 2 femtomoles of target was added. In Experiments 3, 4 and 5, 0.4 femtomoles, 0.08 femtomoles, and 0.016 femtomoles, respectively, of Φ2 SS target were added to the basic solution. In the Control experiment, no target was added.

The samples were boiled for 5 minutes and incubated for 1 hour at 50° C. Each sample was diluted with 400 μl of 5 X SSPE containing 0.1% bovine gammaglobulin (Sigma Chemical Company, St. Louis, Mo.), and 0.1% sodium azide (Aldrich Chemical, Milwaukee, Wis.). One anti-fluorescein-coated bead was added to each solution, and each solution was mixed at 220 rpm for 3 hours at 25° C. Each bead was then washed sequentially in 1 ml of 5 X SSPE for 5 minutes at 25° C. and in 1 ml of 5 X SSPE for 5 minutes at 37° C. Each of the beads was then counted on a scintillation counter. In Table VI, the percentage of sandwich hybridization complexes captured by the bead was calculated to be ($^{32}$P-labelled oligonucleotide A captured by the experimental bead—$^{32}$P-labelled oligonucleotide A captured by the control bead)/(total amount of target present in the experiment) and averaged for two runs of each experiment.

TABLE VI

| Experiment | cpm Captured by Bead | % Complex Captured |
| --- | --- | --- |
| 1 | 13,182 | 53 (± 10) |
| 2 | 2,479 | 48 (± 9) |
| 3 | 630 | 52 (± 11) |
| 4 | 180 | 38 (± 13) |
| 5 | 143 | 53 (± 9) |
| Control | 122 | 0 |

As indicated by the results in Table VI, the immuno-hybridization assay according to the present invention may detect the presence of target DNA in the attomole range as efficiently as in the femtomole range. Thus, the capture efficiency of the sandwich hybridization complex does not appear to be dependent upon the concentration of the target. The sensitivity of this system appears to be limited only by the specific activity of the radioactively-labelled probe. Thus, an immuno-hybridization assay according to the present invention may be used to detect the presence of a very small quantity of DNA with very few manipulations in a short period of time (4 to 5 hours).

In order to increase the sensitivity of the immuno-hybridization assay according to the present invention, a series of experiments was performed wherein a $^{32}$P-labelled nick-translated DNA probe replaced the $^{32}$P-labelled oligonucleotide probe of the previous examples. As indicated in the following Example, the greater length of a nick-translated probe allows a larger amount of label to be attached, so that lower target concentrations may be detected.

EXAMPLE 4

Five experimental mixtures were prepared. In each, a basic solution contained, as first probes, 111 femtomoles of each of 3' fluorescein-labelled oligonucleotides A-1, C-1, D-1, E-1, F-1, G-1, H-1, and J-1; 10 μg of human placental DNa (Sigma Chemical Company, St. Louis, Mo.); and 10 μg of a $^{32}$P-labelled nick-translated plasmid second probe M13mp18 Rf (replicative form, i.e., double-stranded) having a specific activity at the time of use of $1.8 \times 10^8$ cpm/μg in a 5 X SSPE solution diluted from 20 X SSPE. See, Maniatis, et al., *Molecular Cloning*, Cold Spring Harbor Laboratory, 109–112 (1982). To the basic solution, a different amount of target NPE #1 single-stranded DNA was added in each experiment: in Experiment 1, 80 attomoles; in Experiment 2, 16 attomoles; in Experiment 3, 3 attomoles; in Experiment 4, 0.6 attomoles; and in the Control experiment, no target was added.

Each experimental solution was boiled for 5 minutes and then incubated for 17 hours at 50° C. Each sample was diluted with 200 μl of a capture buffer containing 5 X SSC (0.75M NaCl; and 75 mM sodium citrate, pH 7.0); 0.1% non-fat dry milk according to the suggestion of Johnson, et al., *Gene Anal. Techn.*, 1:3–8 (1984); and 0.1% sodium azide. One anti-fluorescein coated bead was added to each of the solutions diluted with capture buffer, and each of the solutions was mixed at 200 rpm for 1 hour at 63° C. The beads were next washed successively in 1 ml of 5 X SSC for 5 minutes at 25° C. and in 1 ml of 5 X SSC for 5 minutes at 63° C. The beads were then counted in a scintillation counter. Two runs of each experiment were averaged to obtain the results as shown in Table VII.

TABLE VII

| Experiment | cpm Captured by Bead | % Complex Captured |
| --- | --- | --- |
| 1 | 2,579 | 5.6 (± 0.7) |
| 2 | 560 | 4.9 (± 0.5) |
| 3 | 220 | 5.0 (± 0.0) |
| 4 | 172 | 9.7 (± 0.0) |
| Control | 138 | 0 |

NPE #1 single-stranded phage DNA has 2.9 kilobases of HSV gD DNA cloned into M13mp18. Thus, it was expected that the fluorescein-labelled first probes would complement portions of the gD sequence and that the second probe would complement portions of the M13mp18 sequence. That these expectations were borne out is indicated in Table VII.

These experiments demonstrate that by increasing the sensitivity of the second probe, accomplished in this example by increasing the amount of label incorporated by the second probe, the limits of the immuno-hybridization assay according to the present invention are expanded. As illustrated above, the use of a $^{32}$P-labelled nick-translated DNA probe allows detection of sub-attomole quantities of target.

In the following example, the feasibility of detecting an immobilized hybridization complex by means of a non-radioactive detection system was explored. In this example, the second probe was 3'-labelled with a biotin group and 5'-labelled with $^{32}$P. The resulting immobilized hybridization complex may be detected by both a radioimmunoassay system and by an enzyme assay system, specifically the avidin:biotinylated Apase Complex discussed in Leafy, et al., *Proc. Natl. Acad. Sci.* (USA), 80:4045 (1983).

EXAMPLE 5

Experiment. A 50 ,1 basal solution was prepared containing a total of 1 picomole of fluorescein-labelled first probes (111 femtomoles each of 3' fluorescein-labelled oligonucleotides A-1, C-1, D-1, E-1, F-1, G-1, H-1, I-1, and J-1); 100 femtomoles of 3 ' biotinylated, 5 ' $^{32}$P-labelled oligonucleotide B-1 as a second probe; 10 femtomoles of NPE #1 as a target; and 10 ,g of human placental DNA (Sigma Chemicals, St. Louis, Mo.) in 5 X SSCE. The basic solution was boiled for 5 minutes and incubated at 63° C. for 1 hour. The solution was diluted with 200 ,1 of capture buffer before adding an anti-fluorescein-coated bead. The bead-containing mixture was incubated at 200 rpm for 1 hour at 63° C. The bead was then washed twice in 1 ml of 0.6 X SSC for 5 minutes at 63° C. and counted in a scintillation counter.

The bead was next incubated in 500 μl of enzyme solution (0.45 μg of biotinylated calf alkaline phosphatase (available from Boehringer Mannhelm, Indianapolis, Ind.), and biotinylated as described in Leafy, et al., supra; 1.35 μg of avidin DN, available from Vector Laboratories, Burlingame, Calif.; 0.5 ml of NMZT buffer (3M NaCl); 1 mM $MgCl_2$; 0.1 mM $ZnCl_2$; and 30 mM triethylanolamine, pH 7.6); and 0.23% bovine serum albumin, available from Sigma Chemical Company, St. Louis, Mo., for 1 hour at 25° C. The enzyme solution was prepared 30 minutes before use. After exposure to the enzyme solution, the bead was washed three times in 1 ml of SCSB buffer (50 mM sodium carbonate-bicarbonate, pH 9.0; 2 µM $ZnCl_2$; 0.5 mM $MgCl_2$; and 0.1M NaCl) for 5 minutes at 25° C.

The bead was then placed in 500 µl of enzyme substrate solution ($10^{-4}$M methylumberliferone phosphate, available from Sigma Chemical Company, St. Louis, Mo., in SCSB buffer) and incubated at 37° C. Ishikawa, et al., *Scand. J. Immunol.*, 8:43 (1978). After 1 hour of incubation, 400 µl of this enzyme substrate solution was mixed with 100 µl of enzyme killing solution (3.0M $K_2HPO_4$, pH 10.4) and analyzed on a Perkin-Elmer 650 S fluorescence detector (excitation 380 mn, emission 445 nm).

Control. A Control experiment mirrored the above Experiment except that no NPE #1 target was present.

The averaged results of two runs of each of Experiment 1 and the control experiment are shown in Table VIII. The "fluorescent units" are those generated by enzyme assay of the hybridization complex.

TABLE VIII

|  | cpm Captured on Bead | % Complex Captured | Fluorescent Units |
|---|---|---|---|
| Experiment | 1,281 | 20 (± 2) | 217 |
| Control | 28 | 0 | 10 |

As indicated by the results shown in Table VIII, the immuno-hybridization assay according to the present invention may be used to quickly detect the presence of small quantities of target DNA by using a non-radioactive enzyme assay.

The feasibility of using an immuno-hybridization assay according to the present invention in order to detect the presence of double-stranded DNA using a non-radioactive detection system was explored in Example 6. Detection of double-stranded DNA is particularly desirable inasmuch as it is in this form that a sample of target DNA is likely to be presented in a clinical setting.

EXAMPLE 6

Experiment. A target was obtained by Sac-1 (New England BioLabs, Beverly, Mass.) restriction endonuclease digestion of BamHI-J plasmid. A 2.9 kilobase fragment containing the gene coding for gDHSV-I was isolated by electrophoresis on agarose gel, followed by electroelution and ethanol precipitation. This fragment was denatured with base in boiling water, neutralized and stored on ice, prior to its use as a target.

A plasmid (pUCgD) containing nine copies of a probing sequence (bases 735–989 of Table I) was prepared by cloning the sequence into a pUC8 plasmid [Bethesda Research Laboratories, Inc., Gaithersburg, Md.] as an EcoRI-HindIII restinction fragment. The gD probing portion of this molecule was exposed by cutting the pUCgD plasmid with HindIII to form a linear probe and by using exonuclease ExoIII [Bethesda Research Laboratories, Inc., Gaithersburg, Md.] to digest the (+) strand of this plasmid revealing 3–4 copies of the probing sequence on the (−) strand. This partially single-stranded DNA was then treated with a biotinylated psoralen derivative to generate a biotinylated second probe.

A 50 ,1 solution was prepared, which solution contained: a total of 1.2 picomole of fluorescein-labelled oligonucleotide first probes; 100 femtomoles of each of A-1, C-1, D-1, E-1, F-1, K-1, L-1,M-1, N-1, R-1, S-1, and T-1; 10 femtomoles of biotinylated second probe; and 20 ,g of human placental DNA (Sigma Chemical Company, St. Louis, Mo.) in 5 X SSCE. To this basic solution was added either 100, 30, 10 or 0 attomoles of target with the "no target" experiment being the control.

The solution was boiled for 5 minutes and incubated at 50° C. for 1 hour. The solution was diluted with 200 ,1 of water and one anti-fluorescein-coated bead was added. This mixture was incubated at 200 rpm for 1 hour at 50° C. The bead was washed with 1 ml of 5 X SSC for 5 minutes at 25° C., with 1 ml of 0.6 X SSC for 5 minutes at 50° C., and counted on a scintillation counter.

In all other respects, a first, second and third Experiment and a Control experiment duplicated the materials and conditions set forth in Example 5.

The average of two runs of each of the Experiments and the Control are set forth in Table IX. In Table IX, the "fluorescent units" are those generated by enzyme assay of the hybridization complex on the anti-fluorescein control bead.

TABLE IX

|  | Attomole of Target | Fluorescent Units |
|---|---|---|
| Experiment 1 | 100 | 487 ± 5.5 |
| Experiment 2 | 30 | 236 ± 18 |
| Experiment 3 | 10 | 191 ± 5.5 |
| Control | 0 | 122 ± 6.6 |

Thus, as is demonstrated by the results in Table IX, the immuno-hybridization system according to the present invention may be used to quickly detect the presence of small quantities of double-stranded target DNA using a non-radioactive enzyme assay.

It is expected that numerous modifications and variations will occur to those skilled in the art upon consideration of the present invention. For example, the component elements necessary to test a sample for the presence of a particular target DNA may be assembled in advance in the form of a kit. Specifically, a first probe complementary to a selected target and bound to a first immunological agent, a second probe bound to a reporter group and complementary to a different portion of the target than the first probe, and a second immunological agent bound to a support may be included in such a kit as separately packaged components. Such a kit may be used to detect the presence of and to quantify the target for which it was designed by combining the probes and support with a sample to be tested for target prepared, for example, according to the procedure of Ranki, et al., *Curr. Top. Microbiol. Immunol.*, 104:317–318 (1983).

Similarly, a kit may be prepared by associated containers of a reporter-bound second probe, a second immunological agent-bound support and a mixture or separate container of several first probes, each being bound to a first immunological agent. Although the sequences of a plurality of first probes may overlap to some extent where required (i.e., different but overlapping), it is particularly desirable from the standpoint of assay sensitivity that the sequence of the second probe be separate (i.e., non-overlapping) from as well as different from that of any first probe in order to ensure that as much immobilized target as possible is labelled.

In addition, although the present invention has been described in terms of a system employing anti-fluorescein coated beads, materials are readily available for practicing the present invention with complexing agents. For example, agarose-bound lectins and biotinylated agarose are available from Vector Laboratories, Inc., Burlingame, Calif. Avidin-coated polymethacrylate spheres and biotin-labelled RNA may be obtained by the procedure of Manning, et al., *Chromosoma (Berl.)*, 53:107–117 (1979).

Therefore, it is intended that the present invention include all such equivalent variations which come within the scope of the invention as claimed.

What is claimed is:

1. A method for immobilizing a target nucleic acid on a solid support consisting essentially of the steps of:

(a) exposing a target nucleic acid to at least two first probes, each first probe having a distinct sequence, each first probe being complementary to a different portion of the target nucleic acid, and each first probe being attached to a support-binding complexing agent;

(b) hybridizing in solution the target nucleic acid with at least one of the first probes and optionally with additional first probes to form a first probe-target nucleic acid hybrid; and (c) attaching, and thereby immobilizing, the first probe-target nucleic acid hybrid to a first probe-binding complexing agent bound to a solid support.

2. The method as recited in claim 1, further comprising the step of introducing a second probe having a sequence complementary to a portion of the target nucleic acid which does not overlap any portion of the target nucleic acid sequence complementary to any first probe, and wherein the second probe is attached to a reporter.

3. The method as recited in claim 1, wherein the target nucleic acid is a double-stranded sequence and wherein the method further comprises the step of making a single-stranded portion of the double-stranded sequence available for hybridization.

4. The method as recited in claim 1, wherein said support-binding complexing agent is an antigen and wherein said probe-binding complexing agent is an antibody.

5. The method as recited in claim 4, wherein said antibody is an anti-fluorescein antibody and wherein said antigen is fluorescein.

6. The method as recited in claim 1, wherein said support-binding complexing agent is biotin.

7. The method as recited in claim 1, wherein said reporter is nonradioactive.

8. The method according to claim 7, wherein said reporter comprises an antigen.

9. The method as recited in claim 1, further comprising the step of separating the solution from the immobilized first probe-target nucleic acid hybrid.

10. A kit for performing a hybridization assay on a sample containing a target nucleic acid, comprising:

(a) at least two first probes, each having a nucleic acid sequence complementary to a portion of a target nucleic acid which is different from a portion to which any other first probe is complementary and wherein each first probe is attached to a first complexing agent;

(b) a second probe having a sequence complementary to a portion of the target nucleic acid different from any portion of said target nucleic acid which is complementary to any first probe and wherein said second probe is attached to a reporter; and (c) a solid support attached to a second complexing agent capable of binding to said first complexing agent.

11. The kit as recited in claim 10, wherein said first complexing agent is an antibody and wherein said second complexing agent is an antigen.

12. The kit as recited in claim 10, wherein said first complexing agent is an antigen and wherein said second complexing agent is an antibody.

13. The kit as recited in claim 10, wherein said first complexing agent is selected from the group consisting of biotin and avidin.

14. The kit as recited in claim 10, wherein said reporter is non-radioactive.

15. The kit as recited in claim 10, said reporter is an antigen.

* * * * *